US00PP24948P3

(12) United States Plant Patent
Shaked et al.

(10) Patent No.: US PP24,948 P3
(45) Date of Patent: Oct. 7, 2014

(54) MEDITERRANEAN MANDARIN TREE NAMED 'HADASS'

(50) Latin Name: ***Citrus deliciosa* Ten (ex *C. reticulata Blanco)***
Varietal Denomination: HADASS

(71) Applicant: State of Israel, Ministry of Agriculture & Rural Development, Agriculture Research Organization, Bet Dagan (IL)

(72) Inventors: Avraham Shaked, Kfar Shmaryahu (IL); Michael Hamou, Rishon Lezion (IL); David Hesdai, Rehovot (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 85 days.

(21) Appl. No.: 13/694,444

(22) Filed: Dec. 4, 2012

(65) Prior Publication Data
US 2014/0157464 P1 Jun. 5, 2014

(51) Int. Cl.
*A01H 5/00* (2006.01)

(52) U.S. Cl.
USPC ..... Plt./202

(58) Field of Classification Search
CPC ..... A01H 1/00; A01H 1/04; A01H 1/06; A01H 4/00; A01H 4/05; A01H 4/008; A01H 5/08; A01H 5/0806
USPC ..... Plt./202
See application file for complete search history.

*Primary Examiner* — Annette Para
(74) *Attorney, Agent, or Firm* — Foley & Lardner LLP

(57) ABSTRACT

A new and distinct mandarin of *Citrus deliciosa* Ten. named 'HADASS', particularly characterized by high internal quality and late ripening.

7 Drawing Sheets

Figure 1:
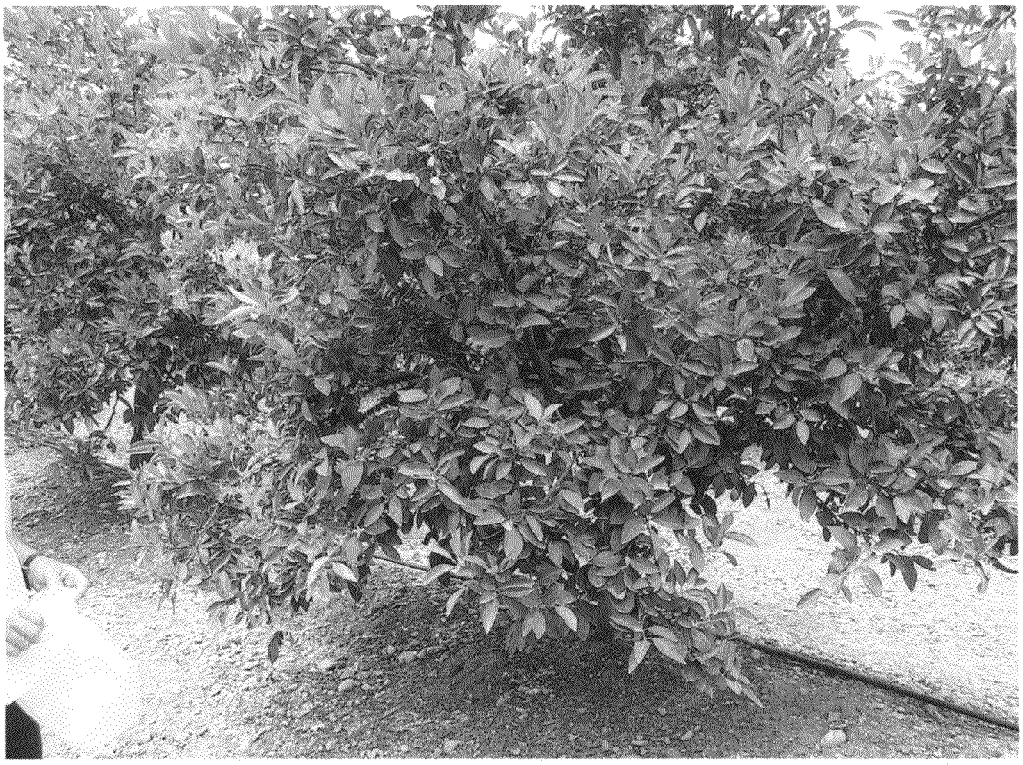

Botanical name of the genus and species of the plant claimed: *Citrus deliciosa* Ten (ex *C. reticulata Blanco*).
Variety denomination: 'HADASS'.

BACKGROUND OF THE INVENTION

The present invention relates to a new and distinct variety of a mandarin tree, botanically known as *Citrus deliciosa* Ten. of the Rutaceae family, and hereinafter referred to by the variety denomination 'HADASS'.

The new *Citrus deliciosa* Ten. variety is a product of a planned breeding program conducted by the inventors, Avraham Shaked, Michael Hamou and David Hesdai, at the Volcani Center, Bet Dagan, Israel. The objective of the breeding program was to develop a new late ripening, *Citrus deliciosa* Ten. variety with high internal quality.

The new *Citrus deliciosa* Ten. variety originated from a selection out of a seedling population, resulting from open pollination of the *Citrus deliciosa* Ten. designated 'ELLENDALE' (unpatented), made by the inventors in 1971 in the Volcani Center, Bet Dagan, Israel. The new *Citrus deliciosa* Ten. 'HADASS' was observed and selected by the inventors within this seedling population in a controlled environment in 1975 in the Volcani Center.

Asexual propagation of the new *Citrus deliciosa* Ten. variety by grafting onto 'Troyer' citrange—*Citrus sinensis* (L.) Osb.×*Poncirus trifoliata* L. (unpatented) was first performed in May 1975 in the Volcani Center, and has demonstrated that the combination of characteristics as herein disclosed for the new variety is firmly fixed and retained through successive generations of asexual propagation. The new variety propagates true-to-type.

BRIEF DESCRIPTION OF THE INVENTION

The following traits have been repeatedly observed and are determined to be characteristics of 'HADASS' which, in combination, distinguish this mandarin tree as a new, unique and distinct variety:

1. High internal quality;
2. Late ripening; and
3. Slightly flattened fruit shape;

In comparison to the parental variety, 'ELLENDALE' (unpatented), 'HADASS' differs primarily in the traits listed in Table 1.

TABLE 1

Comparison with parent variety.

| Trait | New Variety 'HADASS' | Female Parent 'ELLENDALE' (unpatented) |
|---|---|---|
| Time of fruit ripening | very late | mid to late |
| Fruit color of rind | yellow orange | orange-red |
| seed | polyembryonic | monoembryonic |

Of the many commercial varieties known to the present inventors, the most similar to the new *Citrus deliciosa* Ten. 'HADASS' is *Citrus deliciosa* Ten. 'MURCOTT' (unpatented), which differs from the new mandarin 'HADASS' in the characteristics described in Table 2:

TABLE 2

Comparison with a well known commercial variety.

| Characteristic | New Variety 'HADASS' | Comparison Variety 'MURCOTT' (unpatented) |
|---|---|---|
| Time of fruit ripening | Very late | late |
| Fruit size | large | medium |
| Number of seeds | none or very few | many |

BRIEF DESCRIPTION OF THE PHOTOGRAPHS

The accompanying photographs illustrate the overall appearance of the new *Citrus deliciosa* Ten. variety 'HADASS' showing the colors as true as is reasonably possible with colored reproductions of this type. Colors in the photographs may differ slightly from the color values cited in the detailed morphological description, which accurately describe the color of 'HADASS'.

FIG. 1—Shows a flowering tree of 'HADASS'.

Figure 2:
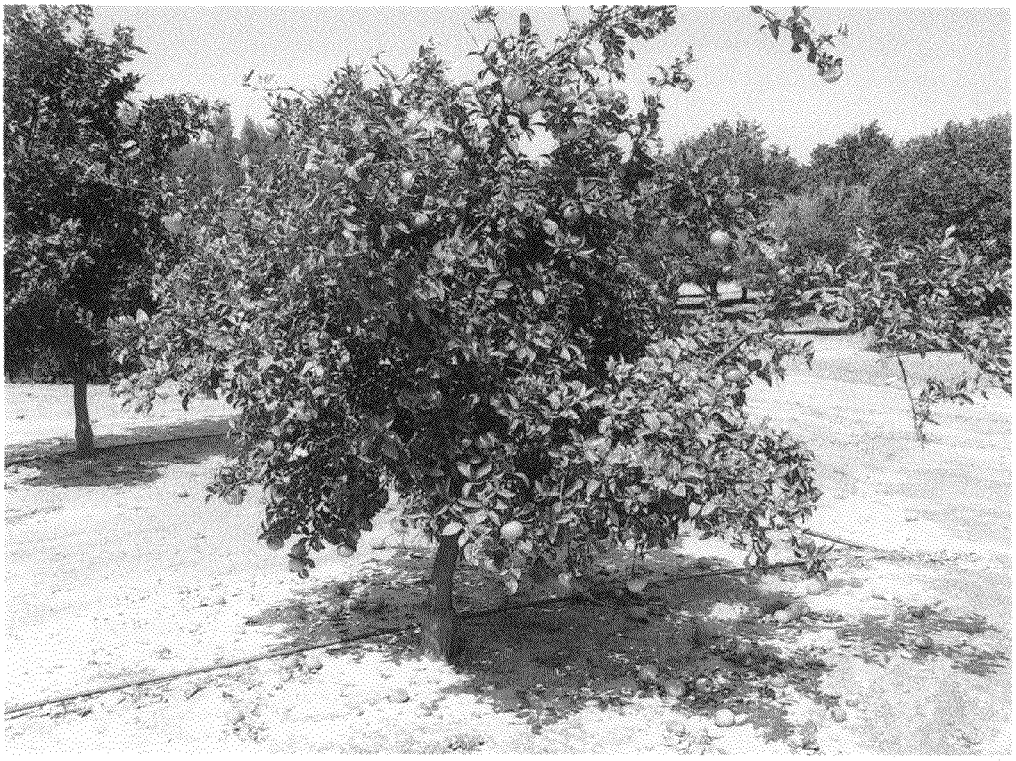

FIG. 2—Shows a fruit-bearing tree of 'HADASS'.

Figure 3:
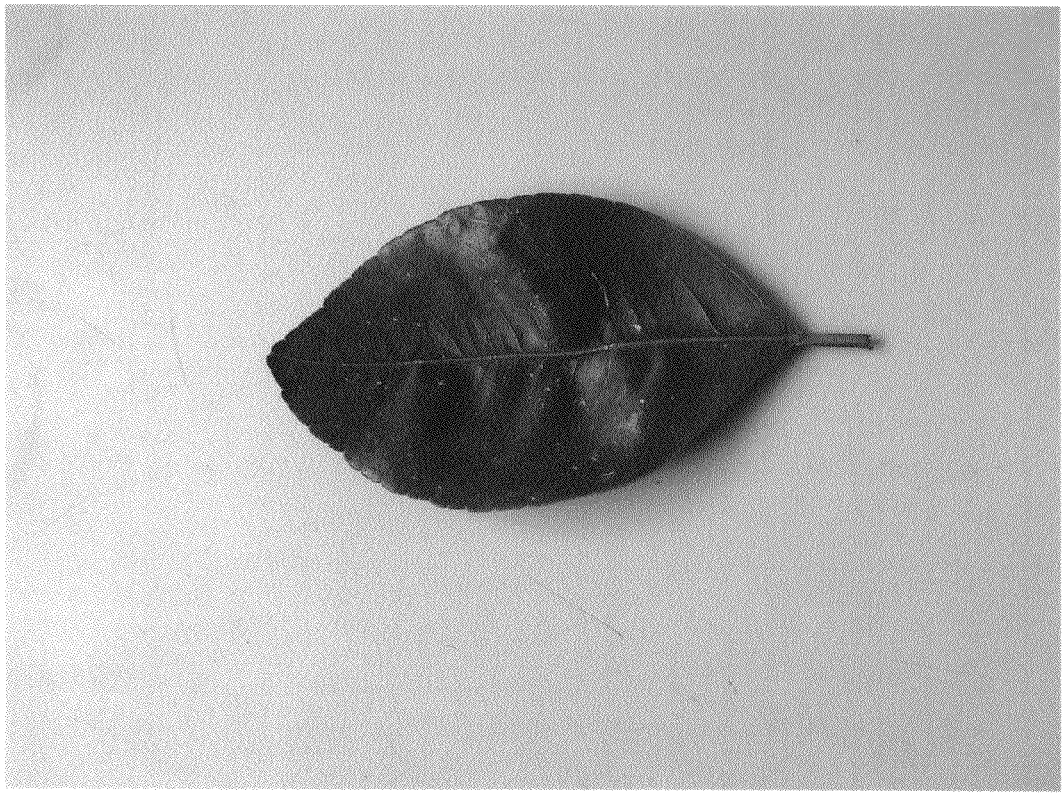

FIG. 3—Shows a typical leaf of 'HADASS'.

Figure 4:
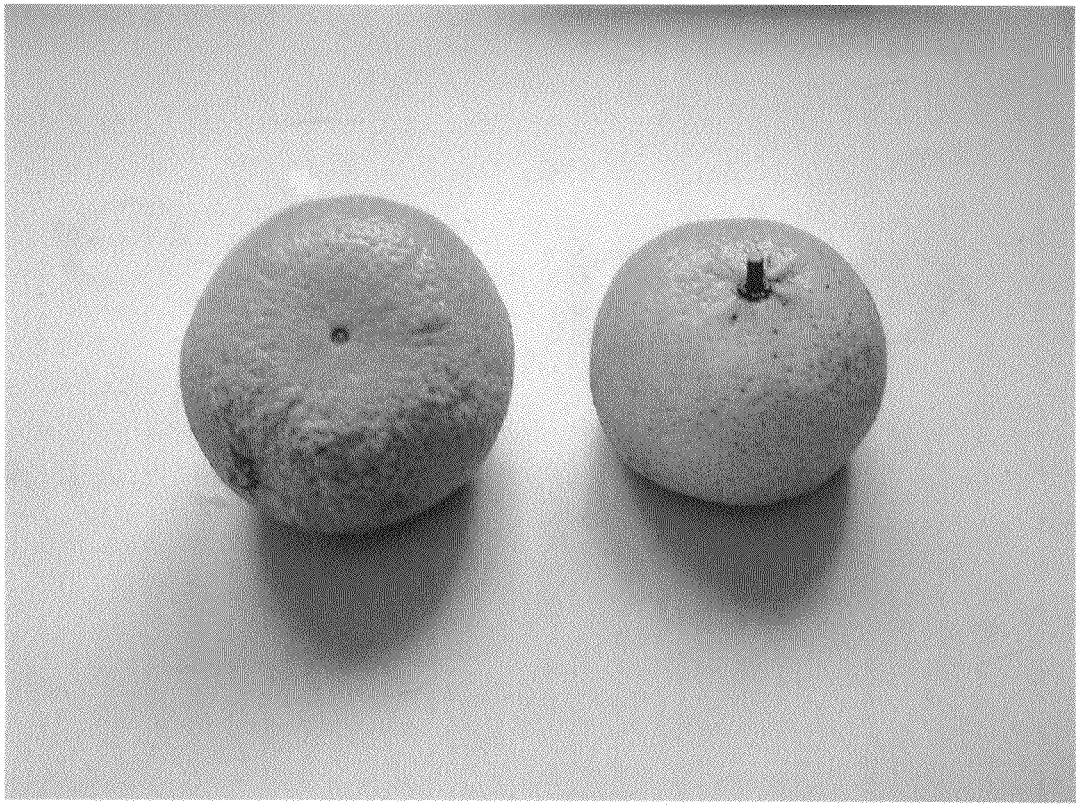

FIG. 4—Shows typical mature fruit of 'HADASS'.

Figure 5:
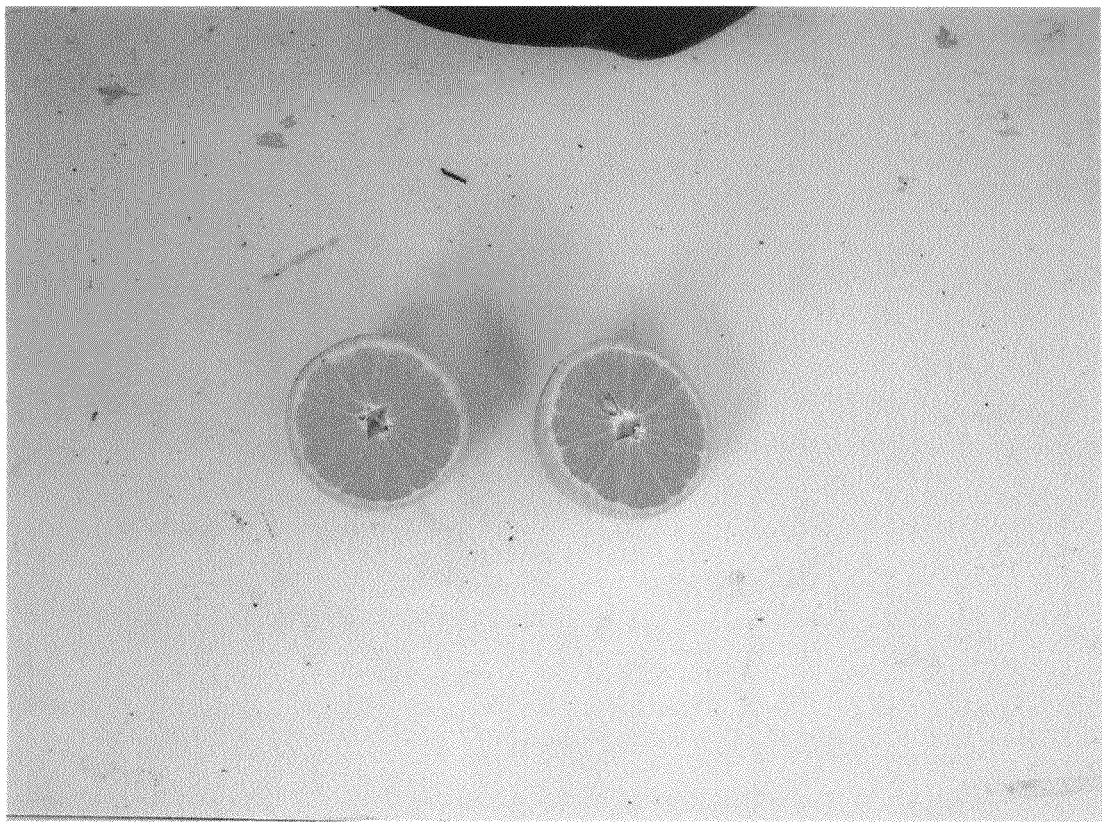

FIG. 5—Shows typical mature fruit of 'HADASS' in cross section.

Figure 6:
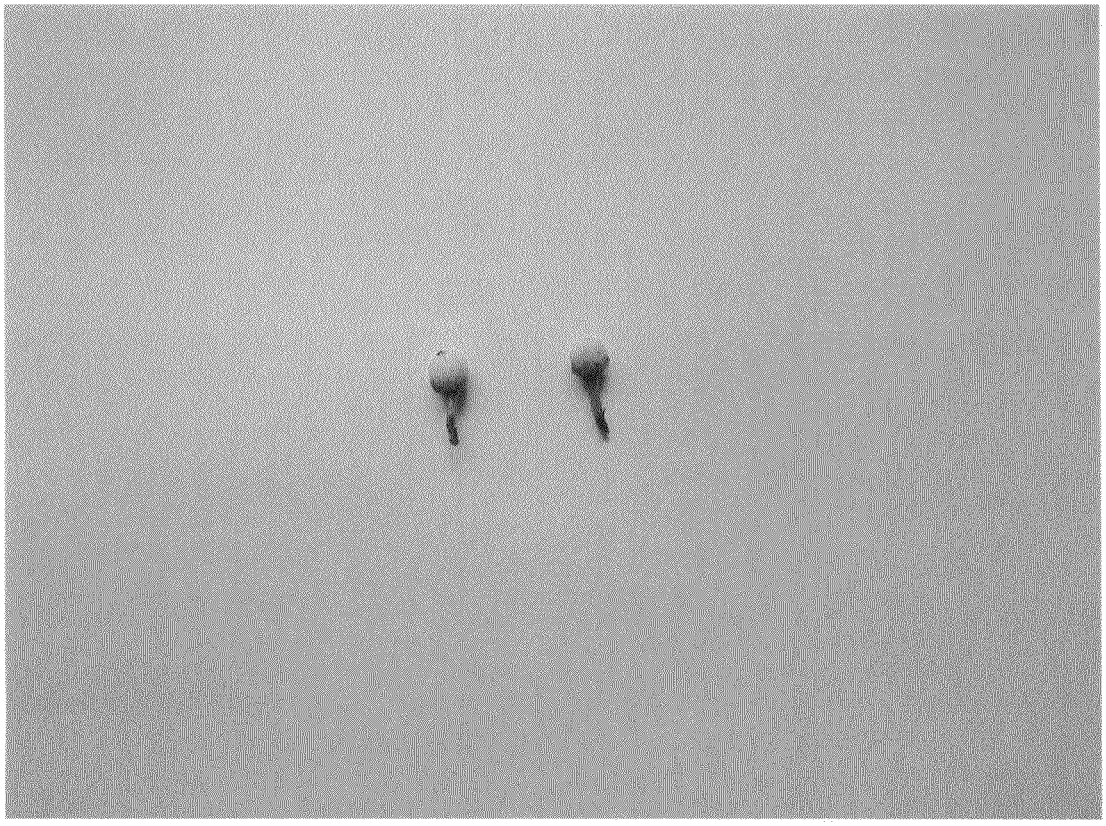

FIG. 6—Shows typical buds of 'HADASS'.

Figure 7:
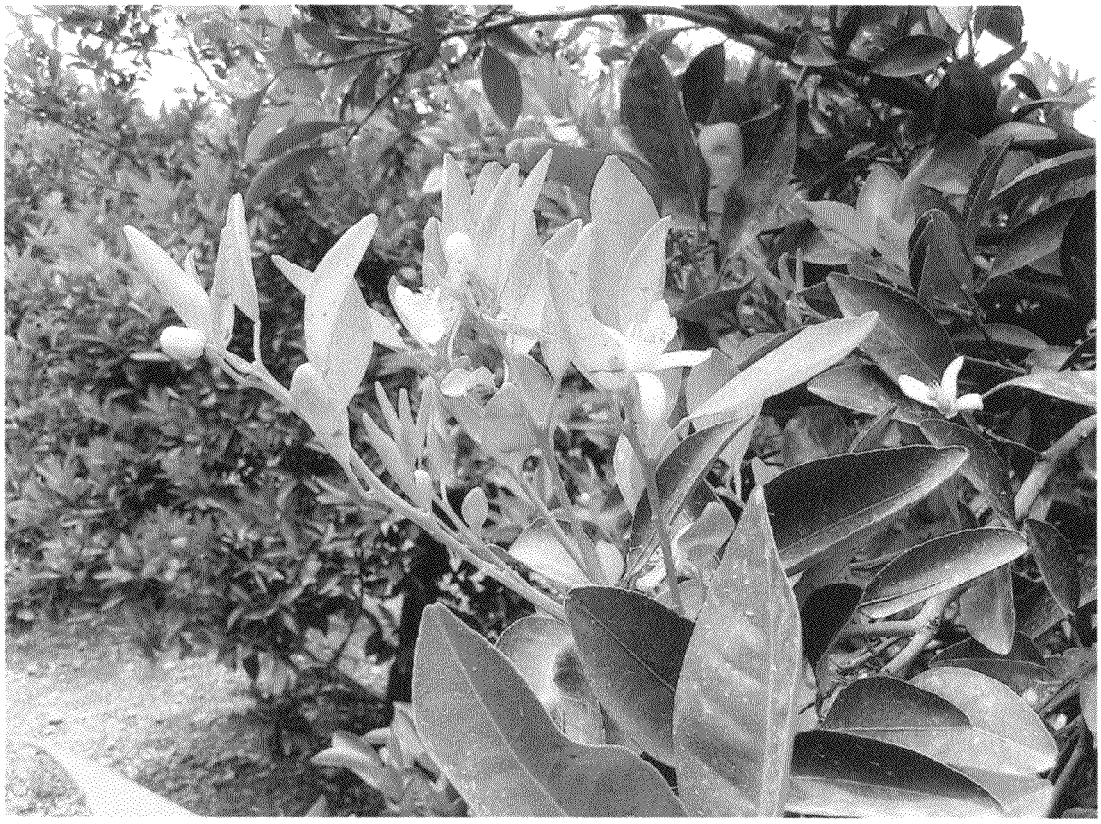

FIG. 7—Shows typical flowers of 'HADASS'.

DETAILED MORPHOLOGICAL DESCRIPTION

The new *Citrus deliciosa* Ten. 'HADASS' has not been observed under all possible environmental conditions. The phenotype of the new variety may vary with variations in environment such as temperature, light intensity, day length, soil or pruning without any change in the genotype of the mandarin plant.

The aforementioned photographs, together with the following observations, measurements and values describe trees of 'HADASS' as grown in the orchard at the Volcani Center, under conditions which closely approximate those generally used in commercial practice. "Pardes", the Hebrew word for citrus orchard, is derived from the Persian "pairidaēza" which means 'surrounded by a wall'. From the same word the word "paradise" was deducted. The described trees were grafted on 'Troyer' citrange—*Citrus sinensis* (L.) Osb.×*Poncirus trifoliata* L. (unpatented) and planted at a distance of 1.5×5 m in sandy red loam soil at an elevation of about 30 meters above sea level with irrigation of 100 $m^3$ per hectare during summer, and addition of 1 liter of fertilizer (N:P:K 7:3:7+micro-elements (trace elements) per 1 $m^3$ of water. Average annual rainfall is about 550 mm, with an average 350 mm of rainfall in winter (December to February). Mean diurnal minimum temperature in January is 7.2° C., and mean diurnal maximum temperature in July is 30.8° C.

Unless otherwise stated, the detailed morphological description includes observations, measurements and values taken from 20111 to 2012 and based on four-year-old 'HADASS' trees grown in the orchard at the Volcani Center. Quantified measurements are expressed as an average or a range of measurements taken from a number of plants of 'HADASS'. The measurements of any individual plant, or any group of plants, of the new variety may vary from the stated average or range.

Color references are made to The Royal Horticultural Society Colour Chart (R.H.S.), (1986), except where general colors of ordinary significance are used. Color values were taken under daylight conditions in full sunlight in the Volcani Center, Bet Dagan, Israel.

All of the plants of 'HADASS', insofar as they have been observed, have been consistent in all the characteristics described below.

Classification:

*Botanical.*—*Citrus deliciosa* Ten.

Parentage:

*Female or seed parent.*—*Citrus deliciosa* Ten. 'ELLENDALE' (unpatented).

Propagation: Grafting onto 'Troyer' citrange — *Citrus sinensis* (L.) Osb.×*Poncirus trifoliata* L. (unpatented).

Growing conditions:

Light intensities: Full sunlight.

| | January | February | March | April |
|---|---|---|---|---|
| Mean maximum air temperature (° C.) | 17.8 | 18.1 | 20.1 | 24.5 |
| Mean minimum air temperature (° C.) | 7.2 | 7.1 | 8.8 | 11.5 |
| Mean rainfall (mm) | 140.5 | 96.9 | 66.1 | 17.5 |
| | May | June | July | August |
| Mean maximum air temperature (° C.) | 27 | 29.2 | 30.8 | 31.2 |
| Mean minimum air temperature (° C.) | 14.6 | 17.9 | 20.6 | 21.2 |
| Mean rainfall (mm) | 2.2 | — | — | — |
| | September | October | November | December |
| Mean maximum air temperature (° C.) | 30.4 | 28.3 | 24.1 | 19.7 |
| Mean minimum air temperature (° C.) | 19.4 | 16 | 11.8 | 8.6 |
| Mean rainfall (mm) | 0.4 | 20.4 | 76.2 | 130.3 |

*Fertilization.*—A balanced fertilizer with level of 7:3:7 (N:P:K)+micro-elements.

*Growth regulators.*—None used.

*Pruning.*—Manual pruning is applied. The size and overall shape of mandarin trees essentially depend on pruning and spacing. 'HADASS' was pruned, creating a tree which is transverse elliptic in shape with 2 or 3 main branches. When the trees are freely grown, the size and the shape assumed by the trees are typical of *Citrus deliciosa* Ten.

TABLE OF CHARACTERISTICS

Tree:

*Age.*—Observed trees were four years old.

*Fruit.*—Type: Mandarin.

*Tree.*—Vigor: strong. Height: about 2 m. Diameter of crown: about 2 m. Overall shape: transverse elliptic. Number of main branches: 2 or 3. Diameter of trunk: about 10 cm. Color of bark: very dark gray closest to RHS 201 A. Surface of bark: nearly smooth. Lenticels: not visible.

*Main branches.*—Length: about 1.5 m. Thickness: about 3 cm. Lenticles: not visible.

*Young leaf.*—Anthocyanin coloration: absent. Upper side green color: medium to dark green RHS 146 AB.

Lower side green color: 146 C. Surface: smooth. Glossiness: absent. Pubescence: absent.

*Fully developed leaf blade*.—Length: 70-90 mm. Width: 40-55 mm. Length/width ratio: longer than broad. Shape in cross section: slightly concave. Twisting: absent. Blistering: medium. Upper side green color: very dark green RHS 147 A. Lower side green color: medium grayish green RHS 147 C. Pubescence on upper side: absent. Pubescence on lower side: absent. Firmness: medium. Undulation of margin: medium. Incision of margin: crenate. Depth of incisions of margin: shallow. Shape of apex: obtuse. Shape of base: obtuse. Glossiness: weak.

*Petiole*.—Length: 7-15 mm. Width of wing: ca. 2 mm. Width of wing relative to blade: very narrow. Shape in cross section: slightly concave. Upper side green color: medium green RHS 146 B. Lower side green color: medium green RHS 146 B. Surface: glabrous

*Petiole wing*.—Upper side green color: very dark green RHS 147 A. Lower side green color: medium grayish green RHS 147 C. Surface: smooth.

*Flower bud*.—Anthocyanin coloration: absent. Shape: cylindrical. Color: medium greenish white RHS 157 A. Length: 5-10 mm. Diameter: 4-6 mm.

*Vegetative bud*.—Anthocyanin coloration: absent. Shape: ellipsoid. Color: medium green RHS 147 B. Length: about 1 mm. Diameter: less than 1 mm.

*Flower*.—No. of petals: 5. Shape: stellate. Diameter of corolla: 17-23 mm. Scent: typical for citrus.

*Pedicel*.—Length: 6-10 mm. Shape in cross section: rounded. Color: light to medium green RHS 146 D. Thickness: about 1 mm.

*Calyx*.—Diameter: 4-5 mm. Color: light green RHS 145 C. Shape: flattened crown. Shape of apex of lobe: acute. Length of lobe: 2-3 mm. Max. width of lobe: ca. 1 mm.

*Petal*.—Shape: elongated. Length: 9-12 mm. Width: 3-5 mm. Color of upper side: white RHS 155 B. Color of lower side: white RHS 155 B.

*Stamina*.—Number: about 20.

*Anther*.—Length: less than 1 mm. Color: very dark yellow RHS 9 A. Shape: elongated.

*Fillament*.—Length: 6-7 mm. Thickness: less than 1 mm. Color: white RHS 155 B.

*Pollen*.—Color: yellow. Viability: present.

*Style*.—Length: 5-6 mm. Diameter: 1-2 mm. Color: light green RHS 145 C.

*Stigma*.—Shape: rounded. Color: very dark yellow RHS 9 A.

*Fruit*.—Weight: about 130 g. Length: 50-60 mm. Diameter: 60-70 mm. Ratio length/diameter: shorter than broad. Position of maximum diameter: in the middle. Shape in cross section: rounded. Shape at stalk end: flattened. Depression at stalk end: absent. Neck: absent. Depression at stalk attachment: slight. Radial grooves at stalk end: few. Length of radial grooves relative to diameter: about half of diameter. Protrusion of collar: not relevant. Floral disc below calyx: absent. Abscission layer between calyx and fruit: absent. Shape at distal end: flattened. Depression at distal end: present. Depth of depression at distal end: very shallow. Diameter of depression relative to fruit: very small. Nipple: absent. Areola: present. Conspicuousness of areola: weak. Type of areola: smooth. Presence of areola: entire. Diameter of areola: 10-20 mm. Stylar scar: present. Diameter of stylar scar: 2-3 mm. Persistence of style: absent. Navel opening: sometimes present. Diameter of navel opening: 2-3 mm. Protrusion of navel: absent. Radial grooves at distal end: absent. Main color of surface: very dark orange RHS 24 A. Pubescence of surface: absent. Glossiness: weak to medium. Roughness of surface: slightly rough. Evenness of size of oil glands: uneven small and large ones. Size of larger oil glands: less than 1 mm. Conspicuousness of larger oil glands: medium. Pebbles on oil glands: sparse. Color of oil glands: dark to very dark orange RHS 24 B. Firmness: firm. Thickness of rind: 1-2 mm. Adherence of rind to flesh: strong. Strength of rind: weak. Oiliness of rind: little. Oil glands on inner side: inconspicuous. Color of albedo: light yellow orange RHS 23 D. Density of albedo: dense. Adherence of albedo to flesh: weak. Number of fibers in albedo: few. Differently colored spots in flesh: absent. Bicolored segments: absent. Main color of flesh: very dark orange RHS 25 A. Filling of core: half filled. Diameter of core: 10-14 mm. Non-developed segments: absent. Number of developed segments: about 11. Open segments: absent. Adherence of segments: medium. Strength of segment wall: medium. Length of juice vesicle: 5-11 mm. Thickness of juice vesicle: 2-3 mm. Conspicuousness of vesicle wall: medium. Adherence of juice vesicles: weak. Presence of navel viewed internally: absent. Strength of fiber: weak. Number of seeds: none or very few when grown in isolation. Poly-embryonic seed: not relevant. Fruit ripening: end of April. Parthenocarpy: present. Time of flowering: March.

TABLE 3 showing the development of fruit maturity.

| DATE | FRUIT WEIGHT | TSS | ACIDITY | TSS/ACIDITY RATIO |
|---|---|---|---|---|
| 02 Mar. 2011 | 641.67 | 13.13 | 1.82 | 7.30 |
| 17 Mar. 2011 | 755.00 | 12.87 | 1.61 | 7.99 |
| 11 Apr. 2011 | 721.67 | 13.00 | 1.14 | 11.48 |

*Maturity*.—Ripe for commercial harvesting; April in Israel.

Disease resistance: No atypical resistance has been noted.

Pest resistance: No atypical resistance has been noted.

Disease susceptibility: None observed.

Pest susceptibility: None observed.

What is claimed is:

1. A new and distinct mandarin variety of *Citrus deliciosa* Ten. named 'HADASS', as illustrated and described herein.

* * * * *